United States Patent

Yamakawa et al.

(10) Patent No.: US 6,515,159 B2
(45) Date of Patent: Feb. 4, 2003

(54) S,S-ETHYLENEDIAMINE-N,N'-DISUCCINIC ACID IRON ALKALI SALT AND A PROCESS FOR PRODUCTION THEREOF

(75) Inventors: Toshitake Yamakawa, Otake (JP); Haruo Sakai, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/931,245

(22) Filed: Aug. 17, 2001

(65) Prior Publication Data

US 2002/0040156 A1 Apr. 4, 2002

Related U.S. Application Data

(63) Continuation of application No. 09/530,275, filed as application No. PCT/JP98/04917 on Oct. 30, 1998, now Pat. No. 6,300,510.

(30) Foreign Application Priority Data

Oct. 31, 1997 (JP) .............................. 9-314562
Dec. 25, 1997 (JP) .............................. 9-366286

(51) Int. Cl.$^7$ ...................... C07F 15/02; C07D 241/02; C07D 241/04
(52) U.S. Cl. ..................... 556/148; 544/384; 544/399
(58) Field of Search .................... 556/148; 544/384, 544/399

(56) References Cited

U.S. PATENT DOCUMENTS

| | | | |
|---|---|---|---|
| 3,158,635 A | 11/1964 | Kezerian et al. | 260/429 |
| 5,679,817 A | 10/1997 | Sakai et al. | 556/148 |
| 6,300,510 B1 * | 10/2001 | Yamakawa et al. | 556/148 |

FOREIGN PATENT DOCUMENTS

| | | | |
|---|---|---|---|
| EP | 694528 | * | 1/1996 |
| JP | 8-34764 | | 12/1994 |
| JP | 10-168045 | | 12/1994 |
| JP | 7-2745 | | 1/1995 |
| JP | 7-291984 | | 11/1995 |
| JP | 07291984 | * | 11/1995 |
| WO | 9428464 | | 12/1994 |

OTHER PUBLICATIONS

Kovaleva et al., "Structural Features of Transit. Metal Compl . . . ", Zh. Neorg. Khim. 37/1, 78–85.

* cited by examiner

Primary Examiner—Mukund J. Shah
Assistant Examiner—Sudhaker B. Patel
(74) Attorney, Agent, or Firm—Fitch, Even, Tabin & Flannery

(57) ABSTRACT

An S,S-ethylenediamine-N,N'-disuccinic acid iron alkali salt which contains a lactam compound represented by the following general formula (1):

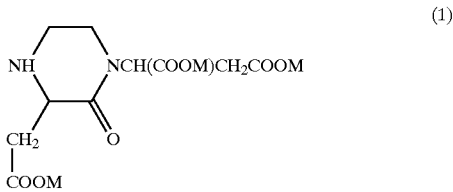

(1)

wherein M is an ammonium ion or an alkali metal ion, and an ethylenediaminemonosuccinic acid represented by the following general formula (2):

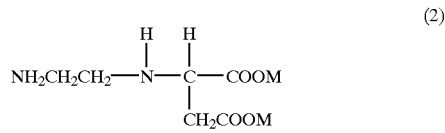

(2)

wherein M is an ammonium ion or an alkali metal ion, in an amount of 7 wt % or less, respectively.

6 Claims, No Drawings

S,S-ETHYLENEDIAMINE-N,N'-DISUCCINIC ACID IRON ALKALI SALT AND A PROCESS FOR PRODUCTION THEREOF

This is a continuation of prior application Ser. No. 09/530,275, filed Apr. 28, 2000, now U.S. Pat. No. 6,300,510 B1, which is hereby incorporated herein by reference in its entirety, which was the national phase of international application PCT/JP98/104917, filed Oct. 30, 1998, which designated the U.S. but was not published English.

TECHNICAL FIELD

The present invention relates to an S,S-ethylenediamine-N,N'-disuccinic acid iron alkali salt that is a chelate compound usable as a photographic bleaching agent, a fertilizer or the like and has little undesirable influence on the environment because of its good biodegradability, and a process for producing said salt.

BACKGROUND ART

The present inventors have disclosed in JP, 8-34764,A that an S,S-ethylenediamine-N,N'-disuccinic acid iron ammonium salt, which is a compound useful for photographic bleaching and the like, has a high biodegradability. However, in a production process for producing the disclosed compound, it was necessary to obtain a highly viscous and highly slurry concentrate because of the very high solubility of the desired compound, in order to obtain the desired compound in high yield. Therefore, there has been a desire for a production process having a higher productivity as an industrial production process. A process for obtaining the desired compound by a concentration to dryness or a continuous hot gas drying has achieved an improvement in the yield but has been disadvantageous in product quality that, for example, powders obtained by said process were so poor in shelf stability that it was colored or was deteriorated in solubility.

Unlike a production process using an inorganic salt such as iron sulfate, a production process using iron oxide was expected to make it possible to obtain a desired compound having a relatively high purity by evaporating a reaction solution to dryness as it was, unless starting materials are decomposed. However, when a meso/racemic mixture of ethylenediamine-N,N'-disuccinic acid was used, a product obtained by such a process had a very high hygroscopic in some cases and moreover its purity was not sufficient. In addition, also when S,S-ethylenediamine-N,N'-disuccinic acid was used, the resulting solid had a low stability, for example, it was colored or gave an insoluble material with a lapse of time. Furthermore, the solid had a low purity and the mass balance of the S,S-ethylenediamine-N,N'-disuccinic acid used was markedly unsatisfactory.

An object of the present invention is to solve such problems and provide an S,S-ethylenediamine-N,N'-disuccinic acid iron alkali salt having a high storage stability and a process for producing the same in high yield.

DISCLOSURE OF THE INVENTION

The present inventors have made extensive studies in order to achieve the above object and consequently found that an S,S-ethylenediamine-N,N'-disuccinic acid iron alkali salt contains an impurity that is difficult to detect even under HPLC analysis conditions under which a slight amount of a chelate compound can be analyzed, because the impurity has a much lower chelate ability than that of other components.

Additionally, the present inventors found that, as a result of various analyses such as mass spectrometry and NMR, the impurity is a compound derived from S,S-ethylenediamine-N,N'-disuccinic acid by a formation of a lactam ring. The present inventors also found that a coloring and a deterioration of a shelf stability of the S,S-ethylenediamine-N,N'-disuccinic acid iron alkali salt are due to the presence of a compound of the following general formula (1) or a compound of the following general formula (2) as reaction by-products and due that an iron complex's stability of these compounds is low that the compounds release a chelated iron with a lapse of time. Thus, the present inventors found that a reduction of an amount of the reaction by-products is important.

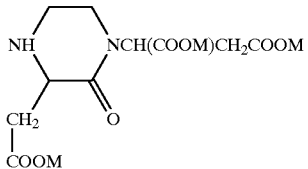

(Wherein M is an ammonium ion or an alkali metal ion.)

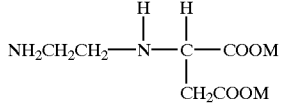

(Wherein n is an ammonium ion or an alkali metal ion.)

In addition, the present inventors found that even if these compounds are contained in the S,S-ethylenediamine-N,N'-disuccinic acid iron alkali salt, this salt is not seriously deteriorated in shelf stability when a content of each of the compounds is 7 wt % or less. The present inventors further found the following: a formation of these impurities can be inhibited by properly controlling a reaction temperature, a reaction period of time and pH at the reaction and adding a reducing agent; of the impurities formed, the lactam compound is easily soluble in a lower alcohol while the S,S-ethylenediamine-N,N'-disuccinic acid iron alkali salt is insoluble therein, and therefore only the impurity can be dissolved by utilizing a difference in solubility between the impurity and the lactam compound; and when a continuous hot gas drying method is adopted, a decomposition of S,S-ethylenediamine-N,N'-disuccinic acid during an oxidation can be minimized, and an oxidation of ferrous iron easily proceeds simultaneously with drying. Thus, the present invention has been accomplished.

That is, one aspect of the present invention is directed to an S,S-ethylenediamine-N,N'-disuccinic acid iron alkali salt which contains a lactam compound represented by the general formula (1) shown below and an ethylenediaminemonosuccinic acid represented by the general formula (2) shown below in an amount of 7 wt % or less, respectively:

(1)

wherein M is an ammonium ion or an alkali metal ion,

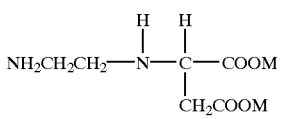

(2)

wherein M is an ammonium ion or an alkali metal ion,

Another aspect of the present invention is directed to a process for producing the above-mentioned S,S-ethylenediamine-N,N'-disuccinic acid iron alkali salt.

BEST MODE FOR CARRYING OUT THE INVENTION

S,S-ethylenediamine-N,N'-disuccinic acid iron alkali salts as such are stable at a room temperature and have a very high water-solubility of 60 g/50 g $H_2O$ or more, and aqueous solutions thereof are weakly acidic substances having a pH of about 5 and can be stably stored.

On the other hand, S,S-ethylenediamine-N,N'-disuccinic acid used as a starting material in a process for producing an S,S-ethylenediamine-N,N'-disuccinic acid iron alkali salt by an iron chelating reaction, is an unstable compound in an acidic solution. It undergoes a lactam ring formation reaction or is decomposed by an amine elimination reaction. Additionally, this compound has a strong acidity of pH 2 or thereabout in an aqueous solution. Therefore, the compound further characterized in that its cyclization gradually proceeds when water is present, without an addition of an acidic substance, even at room temperature. The formation of a cyclization product and a fumaric acid, and a ethylenediaminemonosuccinic acid by an elimination reaction of amine are accelerated by heating.

However, a chelating reaction of iron under basic conditions results in an extreme decrease of a reactivity of iron oxide and a formation of a large amount of iron hydroxide and iron ammine complexes. In addition, when the S,S-ethylenediamine-N,N'-disuccinic acid iron alkali salt is obtained in the form of powder, an alkali present in excess undesirably caused a moisture absorption to deteriorate a stability of a product. Therefore, the reaction was unavoidably carried out with heating in a weakly acidic pH region of 3 to 6, so that the above-mentioned by-products were formed. Furthermore, since these by-products, i.e. the cyclization product and the by-products produced by the amine elimination reaction, have a lower chelate ability than that of S,S-ethylenediamine-N,N'-disuccinic acid, they released iron ions, owing to a pH change, a composition change of liquid caused by additives, and a lapse of time, so that a water-insoluble iron hydrate was formed to cause an appearance of turbidity in an aqueous solution.

The present inventors found the following: an appearance of the turbidity can be prevented to such an extent that it does not cause any problem in practice, by reducing a content of each of the above-mentioned by-products to 7 wt % or less; and the content of each of the by-products can be reduced to 7 wt % or less by taking the countermeasure described below. Thus, the present invention has been accomplished.

Since a formation of the decomposition products and the cyclization product is dependent on a temperature at a chelating reaction of iron or iron oxide with S,S-ethylenediamine-N,N'-disuccinic acid, a reaction period of time and pH at the reaction, a desired compound containing only a slight amount of the by-products can be obtained by making these conditions suitable and adding a stabilizer.

S,S-ethylenediamine-N,N'-disuccinic acid used in the process of the present invention can be synthesized by a known process. For example, this compound can be synthesized either by reacting 1,2-dihaloethane with L-aspartic acid with heating in the presence of an alkali metal hydroxide (Inorganic Chemistry, 7 (11), 2405 (1968)) or by utilizing a microbial enzyme.

As an alkali used in the present invention, ammonia and alkali metals conventionally used in S,S-ethylenediamine-N,N'- disuccinic acid iron alkali salts are preferable. Alkaline earth metals and organic monoamines such as alkylamines may be used as the alkali.

As an iron oxide used in the process of the present invention, any of magnetite, goethite and hematite and the like may be used in the form of powder, magnetite being the most preferable and hematite being the second most preferable. When hematite is used, hematite having a specific surface area of 10 ($m^2/g$) or more, more preferably 15 ($m^2/g$) or more, in terms of BET value is preferable. When magnetite is used, magnetite having a specific surface area of 5 (m /g) or more, more preferably 6 ($m^2/g$) or more, in terms of BET value is preferable. When goethite is used, goethite having a specific surface area of 85 ($m^2/g$) or more, more preferably 95 ($m^2/g$) or more, in terms of BET value is preferable. Here, the term "BET value" means a specific surface area value measured by a low-temperature $N_2$ gas adsorption.

As to the order of charging of starting materials in the process of the present invention, either a method comprising charging an aqueous medium and S,S-ethylenediamine-N,N'-disuccinic acid in a reactor and then adding thereto iron oxide powder, or a method comprising charging an aqueous medium and iron oxide powder in a reactor and then adding thereto S,S-ethylenediamine-N,N'-disuccinic acid may be adopted, the latter being more preferable. As the aqueous medium, either a water or an alcohol-containing water may be used, a water being preferably used.

In the method of charging an aqueous medium and iron oxide powder in a reactor and then adding thereto S,S-ethylenediamine-N,N'-disuccinic acid, a dispersion liquid obtained from the aqueous medium and the iron oxide powder is heated at from 70 to 100° C., preferably from 75 to 95° C., more preferably from 80 to 90° C., and S,S-ethylenediamine-N,N'-disuccinic acid or an S,S-ethylenediamine-N,N'-disuccinic acid monoalkali salt is continuously or intermittently added thereto in the form of powder or a dispersion or solution in an aqueous medium. In this case, pH of the reaction mixture is preferably maintained at from 4.5 to 7, more preferably from 5 to 6.

More particularly, S,S-ethylenediamine-N,N'-disuccinic acid used is mixed with an aqueous alkali solution containing an alkali in an amount of from equivalent to 1.4 moles, preferably from 1.05 to 1.25 moles, per mole of S,S-ethylenediamine-N,N'-disuccinic acid, to obtain a dispersion liquid or aqueous solution of an S,S-ethylenediamine-N,N'- disuccinic acid alkali salt, which is continuously or intermittently added to the iron oxide dispersion liquid. It is also possible to add the S,S-ethylenediamine- N,N'-disuccinic acid powder and the aqueous alkali solution to the iron oxide dispersion liquid separately and continuously or intermittently without beforehand mixing them, to carry out the reaction. In this case, when an addition rate of S,S-ethylenediamine-N,N'-disuccinic acid is rapider than that of the aqueous alkali solution, pH is lowered. Therefore, it is preferable to carry out the reaction while adjusting the pH by adding the aqueous alkali solution so that the pH may be always in a range of 4.5 to 7. Although depending on a reaction temperature, a period of time required for the addition may be properly selected in a range of from 0.2 to 4 hours, preferably from 1 to 3 hours.

Furthermore, a formation of a cyclization product can be inhibited by adding a reducing agent at the time of the chelating reaction. Specific examples of the reducing agent are inorganic reducing agents in the form of powder, wire, ribbon or the like of a metal such as iron powder, zinc powder, magnesium powder, aluminum powder, etc.; and organic reducing agents such as ascorbic acid, isoascorbic acid, oxalic acid, etc. Iron is preferable for suppressing a contamination of a product with impurities. The amount of such additives is 0.1–20 mol %, preferably approximately 1–10 mol %, based on the amount of S,S-ethylenediamine-N,N'-disuccinic acid.

When hematite or goethite is used as the iron oxide, a small amount of a divalent iron exists in a reaction mixture obtained by a dissolution of the iron oxide and a chelation. When magnetite is used, a divalent iron exists in the reaction mixture in an amount of from a few % to over ten % based on the total amount of iron existing in the reaction mixture. For oxidizing the divalent iron into a trivalent iron, a molecular oxygen can be used. When a desired composition is obtained as powder, it is not necessary to introduce a molecular oxygen into the reaction mixture to carry out an oxidation reaction and then dry it which are the conventional procedure. Insoluble materials are removed from the above-mentioned reaction mixture, if necessary, by filtering the reaction mixture and a residue is dried by the use of a continuous hot gas dryer. The divalent iron is effectively oxidized by an air introduced during the drying. Moreover, since a treatment period of time is short, a decomposition of S,S-ethylenediamine-N,N'-disuccinic acid, which has occurred when an air blows into, is inhibited. Therefore, powder of a desired composition can be efficiently obtained. The continuous hot gas dryer includes, for example, a spray dryer and a continuous granulation dryer. A temperature of the hot gas used ranges from 70° C. to 200° C.

S,S-ethylenediamine-N,N'-disuccinic acid iron alkali salt reaction mixture containing of the compounds represented by the above general formula (1) and (2) in an amount of more than 7% is reduced in water content or allowed to assume a dried state, and then the treated reaction mixture is washed with a water-containing lower alcohol, whereby S,S-ethylenediamine-N,N'-disuccinic acid iron alkali salt having intended low contents of the compounds of the general formula (1) and (2) can be efficiently obtained. Examples of the lower alcohol described above include lower alcohols of 1 to 4 carbon atoms. Specific examples thereof include methyl alcohol, ethyl alcohol, isopropyl alcohol, n-propyl alcohol, isobutyl alcohol, tert-butyl alcohol, etc.

Specifically, a water contained in the S,S-ethylenediamine-N,N'-disuccinic acid iron alkali salt reaction mixture containing high contents of the by-products is allowed to evaporate by a concentration under a reduced pressure of the reaction mixture until the water content becomes 60% or less based on the amount of solid components. Then, an absolute or water-containing lower alcohol is added to the residue so as to form a water-containing lower alcohol having a water content of 3 to 35%, preferably 5 to 20%, whereby crystals are dispersed. By separating the crystals by filtration, S,S-ethylenediamine-N,N'-disuccinic acid iron alkali salt having a content of each of the above-mentioned by-products of not more than 7% can be easily obtained.

Another treatment method is as follows: after the reaction mixture is dried with a continuous hot gas dryer, as in spray drying, dried substances can be washed either by dispersing it in a water-containing alcohol having a water content of 3 to 35%, preferably 5 to 20%, followed by a separation by filtration, or by charging the dried substances into a Buchner funnel or the like and rinsing the dried substances with the water-containing alcohol, whereby an S,S-ethylenediamine-N,N'-disuccinic acid iron alkali salt having a content of each of the above-mentioned by-products of not more than 7% can be easily obtained.

The present invention is illustrated in further detail with the following examples and comparative examples, which should not be construed as limiting the scope of the invention.

Iron yield and analysis methods for iron component and a chelate component are as follows.

Iron yield=[(the amount of iron dissolved as determined by a titration)/(the total amount of all iron atoms used in the reaction)]×100

Analysis method for iron component:

All ions of dissolved iron in a sample is converted to ferric iron ions and the thus treated sample is reacted with potassium iodide and then titrated with sodium thiosulfate by using a starch as an indicator.

Analysis method for a chelate component:

An aqueous sodium hydroxide solution is added to an iron complex to eliminate the iron therefrom, and then the resulting substance is dissolved in a solution containing copper to form a copper complex, which is analyzed by a liquid chromatography (column: ODS-2, wavelength: 254 nm, eluent: a buffer solution containing copper, analysis temperature: 40° C.).

EXAMPLE 1

146 g of S,S-ethylenediamine-N,N'-disuccinic acid, 300 g of water and 21 g of 98% sodium hydroxide were charged in a reactor equipped with a stirrer and a thermometer, and were stirred and mixed at room temperature. 37.7 g of magnetite having a BET value of 6.5 ($m^2$/g) and 1.4 g of iron powder were added thereto, and a reaction was carried out with heating and thorough stirring at 80° C. for 2 hours. The contents of by-products in the reaction mixture were as follows: the content of a cyclization product having a lactam ring was 2.7%, and the content of a deamined ethylenediaminemonosuccinic acid was 2%. Insoluble materials were removed from the obtained reaction mixture by filtration, and then the residue was adjusted to pH 5 with S,S-ethylenediamine-N,N'-disuccinic acid. The thus obtained liquid, after a completion of the pH adjustment, was dried with a spray dryer to obtain an S,S-ethylenediamine-N,N'-disuccinic acid iron sodium salt composition having a lactam ring content of 2.5% and an ethylenediaminemonosuccinic acid content of 2%, with an iron yield of 98%.

EXAMPLES 2 to 10

Table 1 shows results obtained by carrying out the reaction in the same manner as in Example 1 except for changing the stabilizer.

TABLE 1

| Examples and Comparative Examples | Kind of Base | Stabilizer | Lactam ring content [%] | Mono-succinic acid content [%] | Iron yield [%] |
|---|---|---|---|---|---|
| Example 2 | Potassium | Iron powder | 2.6 | 2 | 98 |
| Example 3 | Ammonium | Iron powder | 2.6 | 2 | 97 |
| Example 4 | Sodium | Magnesium | 3.1 | 2 | 97 |
| Example 5 | Ammonium | Magnesium | 3.0 | 2 | 96 |
| Example 6 | Sodium | Ascorbic acid | 2.9 | 2 | 97 |
| Example 7 | Ammonium | Ascorbic acid | 3.1 | 2 | 97 |
| Example 8 | Sodium | Oxalic acid | 2.9 | 2 | 97 |
| Example 9 | Ammonium | Oxalic acid | 2.9 | 2 | 98 |
| Example 10 | Ammonium | Formic acid | 6.5 | 5.4 | 93 |
| Comparative Example 1 | sodium | None | 11 | 9 | 90 |

COMPARATIVE EXAMPLE 1

A reaction and after-treatment were carried out under the same conditions as in Example 1 except for adding no stabilizer. Table 1 shows the results obtained.

EXAMPLE 11

A liquid, after a completion of pH adjustment, which had been obtained in Comparative Example 1 was concentrated under a reduced pressure until its water content became 60 wt % based on the weight of the S,S-ethylenediamine-N,N'-disuccinic acid iron sodium salt produced. Methanol of 2, 3 times volume as much as the water contained in the resulting residue was slowly added to the resulting concentrated liquid residue with thoroughly stirring. After a completion of the addition of methanol, the resulting liquid was stirred as it was for 1 hour, and crystals precipitated were filtered and then dried to obtain S,S-ethylenediamine-N,N'-disuccinic acid iron sodium salt in a yield of 80%. In this case, a content of a cyclization product having a lactam ring (a lactam ring content) was 0.5%, and a content of an ethylenediaminemonosuccinic acid was 0.2%.

EXAMPLE 12

One part by weight of a spray-dried S,S-ethylenediamine-N,N'-disuccinic acid iron alkali salt product obtained in Comparative Example 1 was dispersed in 2 parts by volume of ethanol containing 20 vol % of water, and the resulting dispersion was stirred at room temperature for 60 minutes. Then, crystals were separated by filtration and dried to obtain S,S-ethylenediamine N,N'-disuccinic acid iron alkali salt containing 2% of a cyclization product having a lactam ring and 1.5% of an ethylenediaminemonosuccinic acid, in a yield after purification of 80%.

EXAMPLES 13 and 14

Reaction was carried out by the same procedure as in Example 1 except for using goethite having a BET value of 95 (m$^2$/g), or hematite having a BET value of 18 (m$^2$/g), in place of the magnetite having a BET value of 6.5 (m$^2$/g). Table 2 shows the results obtained.

COMPARATIVE EXAMPLES 2 to 4

Reaction was carried out by the same procedure as in Example 1 except for using goethite having a BET value of 80 (m$^2$/g), or hematite having a BET value of 9 (m$^2$/g), in place of the magnetite having a BET value of 6.5 (m$^2$/g). Table 2 shows the results obtained.

TABLE 2

| Examples and Comparative Examples | Kind of Iron | BET value | Lactam ring content [%] | Monosuccinic acid content [%] | Iron yield [%] |
|---|---|---|---|---|---|
| Example 1 | Magnetite | 6.5 | 2.5 | 2 | 98 |
| Example 13 | Goethite | 95 | 4.9 | 3 | 95 |
| Example 14 | Hematite | 18 | 4.5 | 2 | 96 |
| Comparative Example 2 | Magnetite | 4.5 | 10 | 6 | 90 |
| Comparative Example 3 | Goethite | 80 | 12 | 9 | 70 |
| Comparative Example 4 | Hematite | 9 | 10 | 7 | 88 |

EXAMPLE 15

Each of the powders obtained in Examples 1, 10 and 13 and Comparative Examples 1 and 3 was dissolved to obtain a 40% aqueous solution. The solution was stored at 50° C. for 1 week and then diluted to 1% and the dissolution state of the resulting diluted solution was observed. When the crystals obtained in any of Comparative Examples were used, insoluble materials were found. In contrast, when the crystals obtained in any of Examples were used, no insoluble material was found.

EXAMPLE 16

200 g of water, 40 g of magnetite (iron content: 70.5%) and 3 g of iron powder were charged in a 1-liter cylindrical flask equipped with a stirrer, a thermometer and a material feed opening, and were heated at 85° C. Then, 146 g of S,S-ethylenediamine-N,N'-disuccinic acid was dispersed in 365 g of water containing 10.2 g of ammonia, and the resulting dispersion liquid was added to an iron oxide dispersion liquid, which had been beforehand prepared, over about 2 hours by the use of a slurry pump while maintaining a mixture temperature at 80 to 85° C. During the addition, pH of the reaction mixture gradually decreased from 7 and varied in a range of 5.5 to 6. After a completion of the addition, the reaction mixture was maintained at 80° C. for 30 minutes and then cooled to room temperature. This reaction mixture contained a cyclization product having a lactam ring formed in an amount of only 0.5% based on the amount of S,S-ethylenediamine-N,N'-disuccinic acid used and divalent iron ions in an amount of 10% based on the total amount of all iron ions.

Subsequently, insoluble components were removed from the obtained reaction mixture by filtration, and 7g of S,S-ethylenediamine-N,N'-disuccinic acid was added to the liquid residue to adjust the amounts of iron ions and S,S-ethylenediamine-N,N'-disuccinic acid to equimolar. Then, the resulting mixture was dried with a spray dryer to obtain 193 g of an S,S-ethylenediamine-N,N'-disuccinic acid iron ammonium salt containing 0.5% of a compound having a lactam ring and 0.2% of an ethylenediaminemonosuccinic acid, and having a content of divalent iron ions of 0.5% based on all iron ions, and a purity of 98% or more.

EXAMPLE 17

200 g of water, 40 g of magnetite (iron content: 70.5%) and 3 g of iron powder were charged in a 1-liter cylindrical flask equipped with a stirrer, a thermometer and a material feed opening, and were heated at 80° C. Then, 146 g of S,S-ethylenediamine-N,N'-disuccinic acid was added thereto with a spoon over 2.5 hours while maintaining a mixture temperature at 80 to 85° C. During the addition, 150 g of an aqueous solution containing 20.4 g of sodium hydroxide was added to the reaction mixture while adjusting pH of the reaction mixture to 5 to 6. After a completion of the addition, the reaction mixture was maintained at 80° C. for 15 minutes and then cooled to room temperature. The reaction mixture contained a cyclization product having a lactam ring formed in an amount of only 0.4% based on the amount of S,S-ethylenediamine-N,N'-disuccinic acid used. After divalent iron ions remained in an amount of about 8% based on the total amount of all iron ions were oxidized by bubbling air into the reaction mixture, insoluble materials were removed by filtration.

The amount of a compound having a lactam ring in the S,S-ethylenediamine-N,N'-disuccinic acid iron sodium salt aqueous solution thus obtained was 0.4% based on the amount of S,S-ethylenediamine-N,N'-disuccinic acid used.

EXAMPLE 18

200 g of water and 40 g of magnetite (iron content: 70.5%) were charged in a 1-liter cylindrical flask equipped with a stirrer, a thermometer and a material feed opening, and were heated at 85° C. Then, 146 g of S,S-ethylenediamine- N,N'-disuccinic acid was dispersed in 365 g of water containing 10.2 g of ammonia, and the resulting dispersion liquid was added to an iron oxide dispersion liquid, which had been beforehand prepared, over 2 hours by the use of a slurry pump while maintaining a mixture temperature at 80 to 85° C. During the addition, the pH of the reaction mixture gradually decreased from 7 and varied in a range of 5.5 to 6. After a completion of the addition, the reaction mixture was maintained at 80° C. for 30 minutes and then cooled to room temperature. Divalent iron ions remained in the reaction mixture in an amount of about 10% based on the total amount of all iron ions were oxidized by bubbling air into the reaction mixture, and then insoluble materials were removed by filtration. In the solution thus obtained, a cyclization product having a lactam ring was formed in an amount of 0.9% based on the amount of S,S-ethylenediamine-N,N'-disuccinic acid used.

COMPARATIVE EXAMPLE 5

200 g of water, 40 g of magnetite (iron content: 70.5%) and 3 g of iron powder were charged in a 1-liter cylindrical flask equipped with a stirrer, a thermometer and a material feed opening, and were heated at 80° C. Then, 146 g of S,S-ethylenediamine-N,N'-disuccinic acid was added thereto with a spoon over about 2.5 hours while maintaining a mixture temperature at 80 to 85° C. During the addition, 150 g of an aqueous solution containing 20.4 g of sodium hydroxide was added to the reaction mixture while adjusting pH of the reaction mixture at from 3.0 to 4.0, and the whole aqueous sodium hydroxide solution prepared was added at last. After a completion of the addition, the reaction mixture was maintained at 80° C. for 15 minutes and then cooled to room temperature. In this reaction mixture, a cyclization product having a lactam ring was formed in an amount of 2.1% based on the amount of S,S-ethylenediamine-N,N'-disuccinic acid used.

INDUSTRIAL APPLICABILITY

The S,S-ethylenediamine-N,N'-disuccinic acid iron alkali salt of the present invention is a chelate compound usable as a photographic bleaching agent, a fertilizer or the like, and has little undesirable influence on the environment because of its good biodegradability.

What is claimed is:

1. A composition comprising S,S-ethylenediamine-N,N'-disuccinic acid iron alkali salt in an amount of 86 wt % or more but less than 100 wt %, a lactam compound in amount of more than 0 wt % but 7 wt % or less represented by the following general formula (1):

wherein M is an ammonium ion or an alkali metal ion, and an ethylenediaminemonosuccinic acid in amount of 7 wt % or less represented by the following general formula (2):

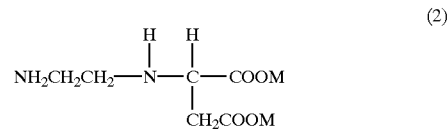

wherein M is an ammonium ion or an alkali metal ion.

2. The composition according to claim 1, wherein the alkali salt in the S,S-ethylenediamine-N,N'-disuccinic acid iron alkali salt is an ammonium salt or an alkali metal salt.

3. The composition according to claim 1, wherein the lactam compound is present in an amount of at least 0.4 wt. %.

4. The composition according to claim 1, wherein the amount of ethylene diaminemonosuccinic acid is present in an amount of at least 0.2 wt. %.

5. A photographic bleaching composition comprising a composition according to claim 1.

6. A fertilizer comprising a composition according to claim 1.

* * * * *